United States Patent
Berg

Patent Number: 6,039,846
Date of Patent: Mar. 21, 2000

[54] SEPARATION OF 3-METHYL-2-PENTENAL FROM N-BUTANOL BY AZEOTROPIC DISTILLATION

[76] Inventor: Lloyd Berg, 1314 S. 3rd Ave., Bozeman, Mont. 59715

[21] Appl. No.: 09/359,614

[22] Filed: Jul. 22, 1999

[51] Int. Cl.$^7$ .............. B01D 3/36; C07C 29/82; C07C 45/84

[52] U.S. Cl. .............. 203/57; 203/58; 203/59; 203/60; 203/63; 203/64; 203/68; 203/70; 203/69; 568/492; 568/913

[58] Field of Search .............. 203/57, 63, 68, 203/70, 69, 64, 59, 58, 60; 568/913, 492

[56] References Cited

U.S. PATENT DOCUMENTS

| | | | |
|---|---|---|---|
| 3,689,371 | 9/1972 | Kerber et al. | 203/37 |
| 4,054,555 | 10/1977 | Ackermann et al. | 568/492 |
| 4,559,111 | 12/1985 | Drake | 203/57 |
| 4,986,885 | 1/1991 | Driscoll et al. | 203/72 |
| 5,064,508 | 11/1991 | Weber et al. | 568/492 |
| 5,362,918 | 11/1994 | Aizawa et al. | 203/68 |
| 5,756,866 | 5/1998 | Rescalli et al. | 568/913 |

FOREIGN PATENT DOCUMENTS 4346959  12/1992  Japan.

*Primary Examiner*—Virginia Manoharan

[57] ABSTRACT

3-Methyl-2-pentenal cannot be separated from 1-butanol by conventional rectification because of the proximity of their boiling points. 3-methyl-2-pentenal can be readily separated from n-butanol by azeotropic distillation. Effective agents are dimethoxymethane, petroleum ether and tetramethylortho-silicate.

1 Claim, No Drawings

SEPARATION OF 3-METHYL-2-PENTENAL FROM N-BUTANOL BY AZEOTROPIC DISTILLATION

FIELD OF THE INVENTION

This invention relates to a method for separating 3-methyl-2-pentenal from n-butanol by azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent. extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

3-Methyl-2-pentenal and n-butanol boil about two degrees apart, have a relative volatility of 1.1 and are difficult to separate by conventional rectification. Table 2 shows that with an agent giving a relative volatilty of 2.7, only twelve actual plates are required.

TABLE 2

Theoretical and Actual Plates Required vs. Relative Volatility for 3-Methyl-2-pentenal-n-Butanol

| Relative Volatilty | Theoretical Plates Required At Total Reflux, 99% Purity | Actual Plates Required, 75% Eff. |
|---|---|---|
| 2.7 | 9 | 12 |
| 2.5 | 10 | 14 |
| 2.0 | 12 | 16 |

OBJECTIVE OF THE THE INVENTION

The object of this invention is to provide a process or method of azeotropic distillation that will enhance the relative volatility of 3-methyl-2-pentenal from n-butanol in their separation in a rectification column. It is a further object of thie invention to identify effective azeotropic distillation agents that are stable and can be recycled.

SUMMARY OF THE INVENTION

The objects of this invention are to provide a process for the separation 3-methyl-2-pentenal from n-butanol which entails the use of certain organic compounds when employed as the agent in azeotropic distillation.

DETAILED DESCRIPTION OF THE INVENTION

I have discovered that certain organic compounds will effectively increase the relative volatility between 3-methyl-2-pentenal and n-butanol during rectification when employed as the agent in azeotropic distillation. They are 2,3-dimethylbutane, decahydronapthalene, t-butyl methyl ether, triethanol amine, trimethylene sulfone, sulfolane 2-nitrotoluene, dimethoxymethane, petroleum ether, tetramethyl ortho silicate, 2,5-diethyl aniline and cyclopentane.

TABLE 3

Effective Azeotropic Distillation Agents For Separating 3-Methyl-2-pentenal From n-Butanol

| Compounds | Relative Volatility |
|---|---|
| None | 1.1 |
| 2,3-Dimethylbutane | 1.7 |
| Decahydronapthalene | 2.0 |
| t-Butyl methyl ether | 1.6 |
| Triethanol amine | 1.4 |
| Trimethylene sulfone | 1.9 |
| Sulfolane | 1.7 |
| 2-Nitrotoluene | 2.2 |
| Dimethoxymethane | 2.3 |
| Petroleum ether | 2.7 |
| Tetramethylortho silicate | 2.9 |
| 2,5-Diethyl aniline | 1.3 |
| Cyclopentane | 1.7 |

THE USEFULNESS OF THE INVENTION

The usefulness or utility of this invention can be demonstrated by referring to the data presented in Tables 1,2 and 3. All of the successful agents show that 3-methyl-2-pentenal can be separated from n-butanol by means of azeotropic distillation and that the ease of of separation is considerable.

WORKING EXAMPLE

Example 1

Fifty grams of 3-methyl-2-pentenal-n-butanol mixture and fifty grams of tetramethylortho silicate as the azeotrope forming agent were charged to a vapor-liquid equilibrium still and refluxed for two hours. The vapor composition was 69.9% 3-methyl-2-pentenal, 30.1% n-butanol; the liquid composition was 44.5% 3-methyl-2-pentenal, 55.5% n-butanol. This is a relative volatility of 2.9.

I claim:

1. A method for recovering 3-methyl-2-pentenal from a mixture of 3-methyl-2-pentenal and n-butanol which consists essentially of distilling a mixture of 3-methyl-2-pentenal and n-butanol in the ptesence of an azeotrope forming agent, recovering the 3-methyl-2-pentenal and the azeotrope forming agent as overhead product and obtaining the n-butanol as bottoms product, wherein said azeotrope forming agent consists essentially of one material selected from the group consisting of 2,3-dimethylbutane, decahydronapthalene, t-butyl methyl-ether, triethanol amine, trimethylene sulfone, sulfolane, 2-nitrotoluene, dimethoxymethane, petroleum ether, tetramethylorthosilicate, 2,5-diethyl aniline and cyclopentane.

* * * * *